United States Patent [19]

Angehrn et al.

[11] 4,431,804
[45] Feb. 14, 1984

[54] THIAZOLYLACETAMIDO COMPOUNDS

[75] Inventors: Peter Angehrn, Böckten; Roland Reiner, Basel, both of Switzerland

[73] Assignee: Hoffmann-La Roche Inc., Nutley, N.J.

[21] Appl. No.: 344,243

[22] Filed: Jan. 29, 1982

[30] Foreign Application Priority Data

Feb. 17, 1981 [CH] Switzerland ............... 1030/81

[51] Int. Cl.³ ........................................... C07D 501/56
[52] U.S. Cl. ....................................... 544/27; 424/246
[58] Field of Search ........................................... 544/27

[56] References Cited
U.S. PATENT DOCUMENTS 4,278,793 7/1981 Durckheimer et al. ............... 544/22
4,327,210 4/1982 Montavon et al. ................... 544/27
4,349,672 9/1982 Montavon et al. ................... 544/27

Primary Examiner—Paul M. Coughlan, Jr.
Attorney, Agent, or Firm—Jon S. Saxe; Bernard S. Leon; Frank P. Hoffman

[57] ABSTRACT

There is provided cephalosporin derivatives of the formula

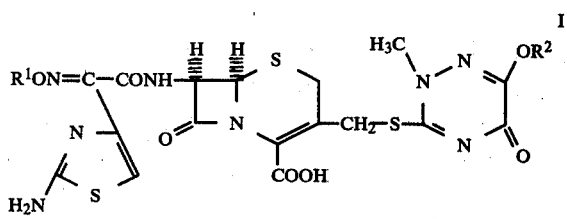

in which
R¹ is carboxy-lower alkyl and
R² is hydrogen, a cation or (with the oxygen atom) a readily hydrolyzable ether group, as well as readily hydrolyzable esters and salts of these compounds and hydrates of the compounds of formula I and of their esters and salts. Also provided are methods for their manufacture and pharmaceutical preparations containing the compounds of formula I.

6 Claims, No Drawings

THIAZOLYLACETAMIDO COMPOUNDS

DESCRIPTION OF THE INVENTION

The present invention is concerned with novel cephalosporin derivatives of the formula

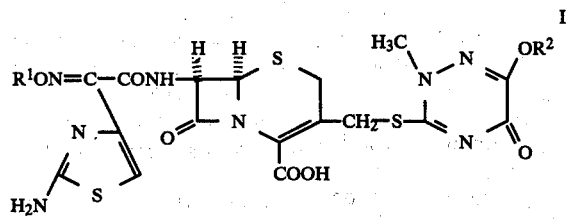

in which
R$^1$ is carboxy-lower alkyl and R$^2$ is hydrogen, a cation or (together with the oxygen atom) a readily hydrolyzable ether group,
as well as readily hydrolyzable esters and salts of these compounds and hydrates of the compounds of formula I and of their esters and salts.

The term "alkyl" or "lower alkyl" used in combination in the present specification represents a straight-chain or branched-chain lower alkyl group containing up to 7, preferably up to 4, carbon atoms; for example, methyl, ethyl, n-propyl, isopropyl, n-butyl, isobutyl, sec-butyl, n-pentyl and n-heptyl. In a "carboxy-lower alkyl" group the carboxy group can be situated on any position of the alkyl group such as, for example, in 1-carboxyethyl, 2-carboxyethyl, 1-carboxy-1-methyl-ethyl, 2-carboxy-1-methyl-ethyl, 1-carboxy-1-methyl-n-propyl and carboxymethyl. 1-Carboxy-1-methyl-ethyl is preferred.

R$^2$ preferably is hydrogen or a cation, but together with the adjacent oxygen atom can also represent a readily hydrolyzable ether group, i.e. a group which is readily hydrolyzable to the hydroxy group. R$^2$ can thus represent, besides hydrogen or a cation, one of the following groups for example: lower alkanoyloxyalkyl (e.g. acetoxymethyl, pivaloyloxymethyl, 1-acetoxyethyl and 1-pivaloyloxyethyl), lower alkoxycarbonyloxyalkyl (e.g. methoxycarbonyloxymethyl, 1-ethoxycarbonyloxyethyl and 1-isopropoxycarbonyloxyethyl) a lactonyl group (e.g. phthalidyl and thiophthalidyl), lower alkoxymethyl (e.g. methoxymethyl) and lower alkanoylaminomethyl (e.g. acetamidomethyl).

As readily hydrolyzable esters of the compounds of formula I there are to be understood compounds of formula I in which the carboxy group is present in the form of a readily hydrolyzable ester group. Examples of such esters, which can be of the conventional type, are the lower alkanoyloxyalkyl esters (e.g. the acetoxymethyl, pivaloyloxymethyl, 1-acetoxyethyl and 1-pivaloyloxyethyl ester), the lower alkoxycarbonyloxyalkyl esters (e.g. the methoxycarbonyloxymethyl, 1-ethoxycarbonyloxyethyl and 1-isopropoxycarbonyloxyethyl ester), the lactonyl esters (e.g. the phthalidyl and thiophthalidyl ester), the lower alkoxymethyl esters (e.g. the methoxymethyl ester) and the lower alkanoylaminomethyl esters (e.g. the acetamidomethyl ester). Other esters (e.g. the benzyl and cyanomethyl esters) can also be used.

Examples of salts of the compounds of formula I are alkali metal salts such as the sodium and potassium salt, the ammonium salt, alkaline earth metal salts such as the calcium salt, salts with organic bases such as salts with amines (e.g. salts with N-ethyl-piperidine, procaine, dibenzylamine, N,N'-dibenzylethylenediamine, alkylamines or dialkylamines) as well as salts with amino acids such as, for example, salts with arginine or lysine. The salts can be di-salts or also tri-salts. The third salt formation (R$^2$=cation) can occur in compounds with the hydroxy group of the 2,5-dihydro-6-hydroxy-2-methyl-5-oxo-as-triazin-3-yl group (i.e. when R$^2$ is hydrogen).

The compounds of formula I also form addition salts with organic or inorganic acids. Examples of such salts are hydrohalides (e.g. hydrochlorides, hydrobromides and hydroiodides) as well as other mineral acid salts such as sulphates, nitrates, phosphates and the like, alkyl-sulphonates and monoarylsulphonates such as ethanesulphonates, toluenesulphonates, benzenesulphonates and the like and also other organic acid salts such as acetates, tartrates, maleates, citrates, benzoates, salicylates, ascorbates and the like.

The compounds of formula I and their salts and readily hydrolyzable esters can be hydrated. The hydration can be effected in the course of the manufacturing process or can occur gradually as a result of the hygroscopic properties of an initially anhydrous product.

The products in accordance with the invention can be present in the syn-isomeric form

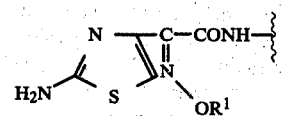

or in the anti-isomeric form

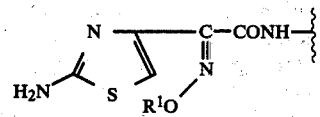

or as a mixture of these two forms. The syn-isomeric form or mixtures in which the syn-isomeric form predominates is/are preferred.

Preferred products are (6R,7R)-7-[(Z)-2-(2-amino-4-thiazolyl)-2-[(1-carboxy-1-methylethoxy)imino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid and its salts as well as the corresponding hydrates.

The aforementioned acyl derivatives can be manufactured in accordance with the invention by (a) reacting a compound of the formula

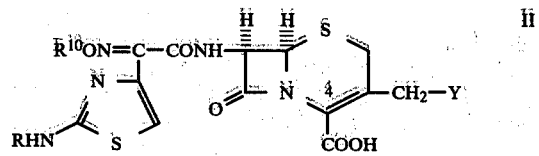

in which
R$^{10}$ is a carboxy-lower-alkyl group optionally protected by salt formation with a base, R is hydrogen or a suitable protecting group, Y is a leaving group and the carboxy group can be protected by salt formation with a base, in the presence of water with a thiol of the formula

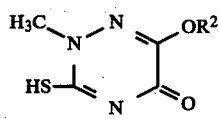

in which $R^2$ is as above,
subsequently cleaving off a protecting group R which may be present and, if desired, converting a salt which may be obtained into the free acid, or (b) for the manufacture of a readily hydrolyzable ester of a compound of formula I, subjecting a carboxylic acid of formula I to a corresponding esterification, or (c) for the manufacture of salts or hydrates or a compound of formula I or hydrates of these salts, converting a compound of formula I into a salt or hydrate or into a hydrate of said salt.

If desired, the carboxy group in the 4-position of the starting material of formula II can be protected by salt formation with a base; for example, by salt formation with an inorganic base such as sodium hydroxide or with a tertiary organic base such as triethylamine. The carboxy-lower-alkyl group $R^{10}$ can be protected in the same manner. Suitable protecting groups denoted by R are those which do not interfere with the reaction of a compound of formula I with the thiol of formula III. Examples of suitable protecting groups denoted by R are protecting groups which are cleavable by acid hydrolysis such as, for example, t-butoxycarbonyl or trityl or protecting groups which are cleavable by basic hydrolysis such as, for example, trifluoroacetyl. Monohalogenated protecting groups such as chloroacetyl, bromoacetyl and iodoacetyl are not suitable for the present thiolation reaction, since they would react with the thiol of formula III.

As the leaving group Y in a starting compound of formula II there come into consideration, for example, halogens (e.g. chlorine, bromine or iodine), acyloxy groups (e.g. lower alkanoyloxy groups such as acetoxy), lower alkylsulphonyloxy or arylsulphonyloxy groups such as mesyloxy or tosyloxy, or the azido group.

The starting materials of formula II can be prepared, for example, by N-acylating the corresponding 7-amino compound, namely by reacting a compound of the formula

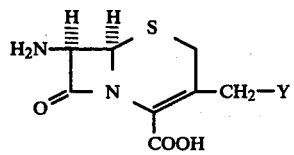

in which
Y is as above and the carboxy group and/or the amino group can be present in protected form,
with an acid of the formula

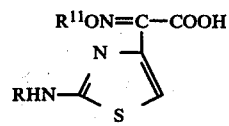

in which

R is as above and
$R^{11}$ is esterified carboxy-lower alkyl,
or with a reactive functional derivative of this acid and, if desired, cleaving off a carboxy protecting group which may be present.

If desired, the carboxy group present in the 7-amino compound of formula IV can be protected in the manner explained above for the starting material of formula II to be prepared or also by esterification, for example, with an aliphatic or araliphatic ester group (e.g. t-butyl) or with a silyl group (e.g. trimethylsilyl). The amino group in the compound of formula IV can be protected, for example, by a silyl protecting group such as trimethylsilyl.

As reactive functional derivatives of acids of formula V there come into consideration, for example, halides (i.e. chlorides, bromides and fluorides), azides, anhydrides, especially mixed anhydrides with strong acids, reactive esters (e.g. N-hydroxysuccinimide esters) and amides (e.g. imidazolides).

The carboxy group in the carboxy-lower alkyl group $R^{11}$ of the acid of formula V or of a reactive functional derivative thereof is present in esterified form; for example, as an aliphatic or araliphatic ester (e.g. the t-butyl ester) or as a silyl ester (e.g. the trimethylsilyl ester).

The reaction of a 7-amino compound of formula IV with the acid of formula V or a reactive functional derivative thereof can be carried out in a manner known per se. Thus, for example, a free acid of formula V can be condensed with one of the aforementioned esters corresponding to formula IV by means of a carbodiimide such as dicyclohexylcarbodiimide in an inert solvent such as ethyl acetate, acetonitrile, dioxan, chloroform, methylene chloride, benzene or dimethylformamide and subsequently the ester group can be cleaved off. Oxazolium salts (e.g. N-ethyl-5-phenyl-isoxazolium-3'-sulphonate) can also be used as the condensation agent in place of carbodiimides.

According to another embodiment, a salt of an acid of formula IV (e.g. a trialkylammonium salt such as the triethylammonium salt) is reacted with a reactive functional derivative of an acid of formula V as mentioned earlier in an inert solvent (e.g. one of the solvents named earlier).

According to a further embodiment, an acid halide, preferably the chloride, of an acid of formula V is reacted with the amine of formula IV. The reaction is preferably carried out in the presence of an acid-binding agent, for example, in the presence of aqueous alkali, preferably sodium hydroxide, or also in the presence of an alkali metal carbonate such as potassium carbonate or in the presence of a lower-alkylated amine such as triethylamine. As the solvent there is preferably used water, optionally in admixture with an inert organic solvent such as tetrahydrofuran or dioxane. The reaction can also be carried out in an aprotic organic solvent such as, for example, dimethylformamide, dimethyl sulphoxide or hexamethylphosphoric acid triamide. When silylated starting materials of formula IV are used, the reaction is carried out in an anhydrous medium.

The reaction of the 7-amino compound of formula IV with the acid of formula V or a reactive functional derivative thereof can conveniently be carried out at temperatures between about $-40°$ C. and room temperature, for example at about $0°-10°$ C.

Protecting groups present in the starting material of formula II (R, $R^{10}$ or on the 4-carboxy group) are preferably cleaved off before carrying out the thiolation in accordance with the invention with the thiols of formula III. It is also possible to cleave off the protecting groups after the thiolation, but in any case an ester group present on the 4-carboxy group should be removed so that the thiolation can be carried out in good yield. The cleavage of the various protecting groups can be carried out not only by acidic but also by alkaline hydrolysis. Acidic hydrolysis, preferably using a lower alkanecarboxylic acid which may be halogenated (e.g. formic acid or trifluoroacetic acid) removes the protecting groups denoted by R which are cleavable by acid hydrolysis (e.g. t-butoxycarbonyl and trityl). Basic hydrolysis, preferably using dilute aqueous alkali hydroxide, removes the protecting groups R which are cleavable by basic hydrolysis (e.g. trifluoroacetyl). The ester protecting groups on $R^{11}$ or on the 4-carboxy group can be cleaved off not only by acidic hydrolysis but also by basic hydrolysis. Silyl protecting groups are readily cleaved off by treatment with water. The temperature at which the cleavage of the various protecting groups is carried out is generally room temperature, although the cleavage can be carried out at a slightly higher or slightly lower temperature (e.g. at about 0° C. to +40° C.).

Subsequently, the thus-liberated carboxy groups can be re-protected, if desired, by treatment with an inorganic or organic base (e.g. with sodium hydroxide, sodium 2-ethylcaproate or triethylamine).

The thiol starting materials of formula III are in tautomeric equilibrium with the corresponding thiones as shown in the following formulae in which $R^1$ is as above:

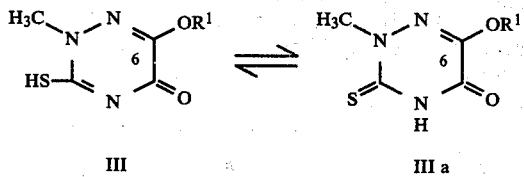

III          III a

The thiol of formula III in which $R^1$ is hydrogen is known. For the preparation of thiols of formula III which are etherified in the 6-position, the $R^1$-group is generally introduced by reacting a S-protected thiol (e.g. by benzhydryl) with the halide containing the $R^1$-group, preferably the iodide, in an inert organic solvent in the presence of an acid-binding agent (e.g. potassium carbonate), preferably at about 10°–50° C., and cleaving off the protecting group (benzhydryl can be cleaved off with anisole and trifluoroacetic acid at room temperature).

The thiolation in accordance with the invention of the starting material of formula II with the thiol of formula III can be carried out in a manner known per se; for example, at a temperature between about 40° and 80° C., conveniently at about 60° C., in water or in a buffer solution having a pH of about 6 to 7, preferably 6.5. A protecting group R which may be present is subsequently cleaved off in the manner described earlier. A salt (mono-, di- or tri-salt, i.e. salt formation is possible on $R^1$, $R^2$ and on the 4-carboxy group) which may be obtained can be converted completely or partially into the free dicarboxylic acid or the free enol ($R^2$=hydrogen) by neutralization with a suitable acid. The acid which can be used for this purpose can be, for example, hydrochloric acid, sulphuric acid, phosphoric acid or citric acid.

In order to manufacture the readily hydrolyzable esters of a dicarboxylic acid of formula I in accordance with variant (b), the dicarboxylic acid is preferably reacted with the corresponding halide, preferably with the iodide, containing the ester group. The reaction can be accelerated with the aid of a base, for example, an alkali metal hydroxide or carbonate or an organic base such as triethylamine. Depending on the amount of esterifying agent used mono- or diesters can be obtained. When the group $OR^2$ is the hydroxy group, this is etherified under these conditions with the formation of a corresponding readily hydrolyzable ether. In this case an excess of the corresponding halide is preferably used. The esterification/etherification is preferably carried out in an inert organic solvent such as dimethylacetamide, hexamethylphosphoric acid triamide, dimethyl sulphoxide or, preferably, dimethylformamide. The temperature preferably lies in the range of about 0°–40° C.

The manufacture of the salts and hydrates of the compounds of formula I or of the hydrates of these salts can be carried out in a manner known per se; for example, by reacting the dicarboxylic acid of formula I with the desired base, conveniently in a solvent such as water or in an organic solvent such as ethanol, methanol, acetone etc. Depending on the amount of base used there can be obtained mono-salts or di-salts. When a compound of formula I in which $OR^2$ is hydroxy is used, salt formation can also take place on this hydroxy group, a tri-salt resulting. The temperature at which the salt formation is carried out is not critical. It is generally carried out at room temperature, but it can also be carried out at a temperature slightly above or below room temperature (e.g. in the range of about 0° C. to +50° C.).

The manufacture of hydrates usually takes place automatically in the course of the manufacturing process or as a result of the hygroscopic properties of an initially anhydrous product. For the controlled manufacture of a hydrate, a completely or partially anhydrous product (carboxylic acid of formula I or ester or salt thereof) can be exposed to a moist atmosphere (e.g. at about +10° C. to +40° C.).

A syn/anti mixture of a compound of formula I which may be obtained can be separated into the corresponding syn- and anti-forms in the usual manner, for example by recrystallization or by chromatographical methods using a suitable solvent or solvent mixture.

The compounds of formula I as well as the corresponding readily hydrolyzable esters and salts or the hydrates of these products have antibiotic, especially bactericidal, activity. They possess a broad spectrum of activity against various gram-positive microorganisms and especially against gram-negative microorganisms, including β-lactamase-forming gram-negative bacteria such as, for example, *Pseudomonas aeruginosa, Haemophilus influenzae, Escherichia coli, Serratia marcescens*, Proteus and Klebsiella species.

The products provided by the invention can accordingly be used for the treatment and prophylaxis of infectious diseases. A daily dosage of about 0.1 g to about 2 g comes into consideration for adults. The parenteral administration of the compounds provided by the invention is especially preferred.

In order to demonstrate the antimicrobial activity of the products provided by the invention, a representative member, namely the trisodium salt of (6R,7R)-7-[(Z)-2-(2-amino-4-thiazolyl)-2-[(α-carboxy-1-methylethoxy)imino]-acetamido]-3-[[(2,5-dihydro-6-hydroxy-2-methyl-5-oxo-as-triazin-3-yl)thio]methyl]-8-oxo-5-thia-1-azabicyclo[4.2.0]-oct-2-ene-2-carboxylic acid was tested for its in vitro activity against 15 strains of the human-pathogenic disease-causing organism *Pseudomonas aeruginosa*.

Results (as MIC = minimum inhibitory concentration in μg/ml):

| Designation of the strain of P. aeruginosa | MIC μg/ml |
|---|---|
| 1 | 6.3 |
| 2 | 1.6 |
| 3 | 1.6 |
| 4 | 1.6 |
| 5 | 1.6 |
| 6 | 1.6 |
| 7 | 1.6 |
| 8 | 25 |
| 9 | 3.1 |
| 10 | 1.6 |
| 11 | 0.8 |
| 12 | 1.6 |
| 13 | 1.6 |
| 14 | 1.6 |
| 15 | 1.6 |

Toxicity of the trisodium salt of (6R,7R)-7-[(Z)-2-(2-amino-4-triazolyl)-2-[(1-carboxy-1-methylethoxy)imino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid:

| $LD_{50}$, mg/kg | i.v. > 1000 |
|---|---|
| | s.c. > 4000 |
| | p.o. > 4000 |

The products provided by the invention can be used as medicaments, for example in the form of pharmaceutical preparations which contain them in admixture with a pharmaceutical, organic or inorganic inert carrier material which is suitable for enteral or parenteral administration such as, for example, water, gelatine, gum aragic, lactose, starch, magnesium stearate, talc, vegetable oils, polyalkyleneglycols, Vaseline etc. The pharmaceutical preparations can be made up in solid form (e.g. as tablets, dragees, suppositories or capsules) or in liquid form (e.g. as solutions, suspensions or emulsions). If necessary, the pharmaceutical preparations can be sterilized and/or can contain adjuvants such as preserving, stabilizing, wetting or emulsifying agents, salts for varying the osmotic pressure, anaesthetics or buffers. They can also contain other therapeutically valuable substances. The compounds of formula I in which $R^2$ is hydrogen and their salts or hydrates are preferably administered parenterally and for this purpose are preferably prepared as lyophilizates or dry powders for dilution with customary agents such as water or isotonic sodium chloride solution. The corresponding readily hydrolyzable esters or their salts or hydrates can also be administered enterally.

The following Examples illustrate the present invention:

EXAMPLE 1

Manufacture of the trisodium salt of (6R,7R)-7-[(Z)-2-(2-amino-4-thiazolyl)-2-[(1-carboxy-1-methylethoxy)imino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid.

17.13 g of the disodium salt of (6R,7R)-3-(acetoxymethyl)-7-[(Z)-2-(2-amino-4-thiazolyl)-2-[(1-carboxy-1-methylethoxy)imino]acetamido]-8-oxo-5-thia-1-azabicyclo[4.2.0]oct-2-ene-2-carboxylic acid are dissolved in 200 ml of water and treated with 5.25 g of tetrahydro-2-methyl-3-thioxo-as-triazine-5,6-dione. The mixture is stirred for 10 hours at 55°–60° C. while gassing with nitrogen, the pH being held at 6.5 by means of an autotitrator. The reddish solution is cooled to 25° and diluted with 150 ml of water. The pH is adjusted to 3.8 with about 62 ml of 1 N hydrochloric acid while stirring. The precipitated material is filtered off under suction, washed with 50 ml of water, sucked dry well and dried at 25° C. in vacuo. There is obtained a brownish Fraction I which is discarded. The combined mother liquor and wash-water (yellow-orange) are adjusted to pH 3 with about 38 ml of 1 N hydrochloric acid while stirring. The precipitated material is filtered off under suction, washed with 100 ml of water, sucked dry well and dried at 25° C. in vacuo. There is obtained a beige Fraction II which, for the formation of the trisodium salt, is treated in 1500 ml of methanol with 30 ml of a 2 N solution of sodium 2-ethylcaproate in ethyl acetate. The mixture is stirred for 15 minutes, a solution resulting. After adding ethanol until a slight turbidity occurs, the mixture is concentrated strongly in vacuo at 40° C., whereby substance precipitates. This substance is filtered off under suction, washed successively with ethanol and low-boiling petroleum ether and dried at 45° C. overnight in a high vacuum. Thereafter, the substance is equilibrated in the air for a further 1 hour. There is obtained beige, amorphous title substance with $[\alpha]_D^{20} = -81°$ (c=1 in water). The nuclear resonance spectrum corresponds to the given structure.

The disodium salt of (6R,7R)-3-(acetoxymethyl)-7-[(Z)-2-(2-amino-4-thiazolyl)-2-[(1-carboxy-1-methylethoxy)imino]acetamido]-8-oxo-5-thia-1-azabicyclo[4.2.0]oct-2-ene-2-carboxylic acid used as the starting material can be prepared as follows:

5.72 g of 2-(tritylamino)-4-thiazolepyruvic acid (Z)-O-[1-(tert-butyoxycarbonyl)-1-methylethyl] oxime and 3.28 g of 7-aminocephalosporanic acid tert-butyl ester are added to a mixture of 1 ml of pyridine and 100 ml of dichloromethane at 25° C. 2.27 g of dicyclohexylcarbodiimide are added to the resulting solution. The mixture is stirred at 25° C. for 1 hour, dicyclohexylurea precipitating. This is filtered off and the yellow filtrate is evaporated at 40° C. in vacuo. The residue is taken up in 100 ml of ethyl acetate, washed successively with 50 ml of 1 N hydrochloric acid, 50 ml of dilute sodium chloride solution and 50 ml of saturated sodium hydrogen carbonate solution, dried over sodium sulphate and evaporated at 40° C. in vacuo. The evaporation residue obtained is a crude yellowish foam which is purified on a silica gel column using ether for the elution. The fractions containing the desired product are pooled and evaporated in vacuo. The residual foam is boiled up in 200 ml of isopropyl ether, the substance firstly passing into solution and shortly thereafter crystallizing out. The mixture is left to cool to 25° C. The crystallizate is filtered off under suction, washed successively with isopropyl ether and low-boiling petroleum ether and dried at 40° C. overnight in a high vacuum. There is obtained (6R,7R)-3-(acetoxymethyl)-7-[(Z)-2-[[1-(tert-butoxycarbonyl)-1-methylethoxy]imino]-2-[2-(tritylamino)-4-thiazolyl]acetamido]-8-oxo-5-thia-1-azabicyclo[4.2.0]oct-2-ene-2-carboxylic acid tert-butyl ester as white crystals with $[\alpha]_D^{25} = +5.6°$ (c=1 in dimethyl sulphoxide). The nuclear resonance spectrum and the microanalysis correspond to the given structure.

62 g of (6R,7R)-3-(acetoxymethyl)-7-[(Z)-2-[[1-(tert-.butoxycarbonyl)-1-methylethoxy]imino]-2-[2-(tritylamino)-4-thiazolyl]acetamido]-8-oxo-5-thia-1-azabicyclo[4.2.0]oct-2-ene-2-carboxylic acid tert-butyl ester are dissolved in 500 ml of trifluoroacetic acid. After stirring at 25° C. for 1.5 hours, the solution is evaporated at 40° C. in vacuo. The residue is evaporated at 40° C. for 2 hours in a high vacuum with the use of a dry-ice condenser. The residual yellow-brown foam is dissolved in 500 ml of pure formic acid. 150 ml of water are added to this solution and the mixture obtained is stirred at 25° C. for 1.25 hours. A further 500 ml of water are added to the mixture. The precipitated triphenylcarbinol is separated by filtration. The yellowish-brown filtrate is evaporated at 40° C. in vacuo. The oily residue is treated with 200 ml of water. A small amount of brown undissolved material is filtered off and discarded. The yellowish-brown filtrate is lyophilized overnight. There is obtained a yellowish-lyophilizate which, for the formation of the disodium salt, is dissolved in 600 ml of methanol and treated with 100 ml of a 2 N solution of sodium 2-ethylcaproate in ethyl acetate. After adding 600 ml of ethanol until slight turbidity occurs, the mixture is concentrated strongly at 40° C. in vacuo, whereby substance precipitates. This substance is filtered off under suction, washed successively with ethanol and low-boiling petroleum ether and dried at 40° C. overnight in vacuo. A beige Fraction I is obtained. The mother liquor is combined with the washethanol, the mixture is treated with 500 ml of ethanol and again concentrated at 40° C. in vacuo. The material which precipitates in amorphous form is filtered off under suction, washed successively with ethanol and low-boiling petroleum ether and dried at 40° C. overnight in vacuo. A light beige Fraction II is obtained. For purification, the combined Fractions I and II are dissolved in 500 ml of methanol, treated with 25 ml of a 2 N solution of sodium 2-ethylcaproate in ethyl acetate and the mixture is diluted with 750 ml of ethanol. The brownish material which thereby precipitates in amorphous form is filtered off and discarded. The dark yellow filtrate is concentrated strongly at 40° C. in vacuo, diluted with 500 ml of ethanol and again concentrated at 40° C. in vacuo. The material which thereby crystallizes out is filtered off under suction, washed successively with ethanol and low-boiling petroleum ether and dried at 40°–45° C. overnight in a high vacuum. There is obtained the disodium salt of (6R,7R)-3-(acetoxymethyl)-7-[(Z)-2-(2-amino-4-thiazolyl)-2-[(1-car-boxy-1-methylethoxy)imino]acetamido]-8-oxo-5-thia-1-azabicyclo[4.2.0]oct-2-ene-2-carboxylic acid as yellowish crystals with $[\alpha]_D^{25} = +40.7°$ (c=1 in water). The nuclear resonance spectrum corresponds to the given structure.

EXAMPLE 2

Production of dry ampoules for intramuscular administration:

A lyophilizate of 1 g of the trisodium salt of (6R,7R)-7-[(Z)-2-(2-amino-4-thiazolyl)-2-[(1-carboxy-1-methylethoxy)imino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid is prepared in the usual manner and filled into an ampoule. Prior to the administration, the lyophilizate is treated with 2.5 ml of a 2% aqueous lidocaine hydrochloride solution.

What is claimed:

1. A compound of the formula

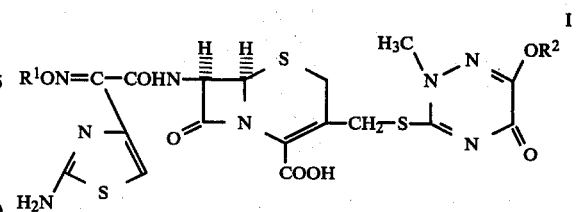

in which

R$^1$ is carboxy-lower alkyl and R$^2$ is hydrogen, a cation or (with the oxygen atom) a readily hydrolyzable ether group selected from the group consisting of lower alkanoyloxyalkyl, lower alkoxycarbonyloxy alkyl, a lactonyl group, lower alkoxymethyl and lower alkanoylaminomethyl as well as readily hydrolyzable esters selected from the group consisting of lower alkanoyloxy alkyl, lower alkoxycarbonyloxyalkyl, lactonyl, lower alkoxymethyl and lower alkanoyl aminomethyl esters and salts of these compounds and hydrates of the compounds of formula I and of their esters and salts.

2. The compound of claim 1 in which the compound is in the syn-isomeric form or in the form of mixtures in which the syn-isomeric form predominates.

3. The compound of claim 2, wherein R$^1$ is 1-carboxy-1-methylethyl.

4. The compound of claim 3, wherein R$^2$ is hydrogen.

5. The compound of claim 4, wherein the compound is a trisodium salt.

6. The compound: (6R,7R)-7-[(Z)-2-(2-Amino-4-thiazolyl)-2-[(1-carboxy-1-methylethoxy)imino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid as well as salts of this compound and hydrates of this compound or salts.

* * * * *